US005518722A

United States Patent [19]
Szalóki et al.

[11] Patent Number: 5,518,722
[45] Date of Patent: May 21, 1996

[54] SKIN REGENERATING COSMETIC COMPOSITION

[75] Inventors: Erzébet Szalóki; Éva Szabó; Éva Hegedüs; Erika Jacsó; Irén Hangácsi; Kálmán Kerek; Erzsébet Bereczki; Erzsébet Sas; Túnde Szabó; Erika Karancsi, all of Debrecen; Ágnes Fábián, Budapest; Zsolt Ágni, Debrecen; Gabriella Papp, Debrecen; Anikó Kovács, Debrecen; Ilona Nagy, Debrecen; Túnde Jakab, Debrecen; Gabriella Demkó, Debrecen; Erika Apagyi, Debrecen, all of Hungary

[73] Assignee: Biogal Gyógyszergyár Rt, Debrecen, Hungary

[21] Appl. No.: 222,371

[22] Filed: Mar. 28, 1994

[60] filed as PCT/HU93/00042, Jul. 1, 1993

[30] Foreign Application Priority Data

Jul. 28, 1992 [HU] Hungary ........................ 9202470

[51] Int. Cl.$^6$ .............. A61K 35/78; A61K 7/48
[52] U.S. Cl. .................... 424/195.1; 424/401
[58] Field of Search ............... 424/401, 195.1; 514/844, 846, 937

[56] References Cited

U.S. PATENT DOCUMENTS

| 4,601,905 | 7/1986 | Széles | 424/195.1 |
| 4,950,481 | 8/1990 | Kéri et al. | 424/195.1 |

FOREIGN PATENT DOCUMENTS

| 184410 | 6/1987 | Hungary . |
| 195420 | 12/1988 | Hungary . |
| 195915 | 2/1989 | Hungary . |

*Primary Examiner*—Jyothsan Venkat
*Attorney, Agent, or Firm*—Schweitzer Cornman & Gross

[57] ABSTRACT

A skin regenerating composition which comprises as active ingredients a mixture of skin regeneratingly effective amounts each of an extract of the plants chickweed and pansy.

11 Claims, No Drawings

SKIN REGENERATING COSMETIC COMPOSITION

FIELD OF THE INVENTION

The invention relates to skin regenerating synergistic cosmetic compositions.

BACKGROUND OF THE INVENTION

Human skin is damaged to an ever increasing degree by environmental effects, air pollution, and lack of suitable residential microclimate. In milder cases such damage takes the form of pathologically dry, inflamed, scurfy, itching skin formations, and lesions. When the skin problems are more serious, dermatologists suggest the use of pharmaceutical compositions generally containing synthetic active ingredients.

In cases of relatively milder skin damage, various paramedicinal or cosmetic composition are recommended in the literature to ameliorate the symptoms. Such a composition is described for example in Hungarian patent No. 195,420 which contains extracts of St. John's wort and marigold, tocopherol, collagen, allantoin, panthenol, jojoba oil, chamomile oil and chamomile extract.

According to Hungarian patent No. 195,915 the extract of different parts of the maize plant prepared with water or with water miscible pharmaceutically acceptable organic solvents is formulated together with the usual excipients, diluents or vehicles to form a skin regenerating and hydrating cosmetic composition.

A topical composition having a somewhat similar effect is described in Hungarian patent No. 184,410, which contains as active ingredient the aqueous or ethanolic extracts of drugs of species belonging to the Fagaceae and/or Chenopodicae and/or Rosaceae families.

Due to the great variety of symptoms, the different sensitivity of the individuals, and the potential allergic skin reactions, no composition is known which could be generally applied for all varieties within the above group of symptoms.

DESCRIPTION OF THE INVENTION

The aim of our work was to create a new, synergistic composition free of harmful side effects, comprising essentially natural active ingredients, suitable for the treatment of pathologically dry, inflamed, scurfy, itching skin formations and lesions, and in milder cases, eczema and acne of the type which normally do not require medical intervention.

We have surprisingly found that the above aims can be accomplished with a composition comprising as active ingredient extracts a plant of the family Caryophyllacae (i.e. the Pink family) and pansy (Fiola tricolor).

The Caryophyllaceae drug of the plant from the Pink family is the above ground part of the plant collected in time of flowering. The main active ingredients of the drug are volatile oils, organic and inorganic salts, and saponines. In case of internal use its antiphlogistic, blood-clearing, antipyretic, expectorating and antitussive effects are known. Its oily extract is suitable for the topical treatment of eruptions and certain types of psoriasis. A particularly suitable member of the Caryophylacae for use in accordance with the present invention in the dianthus known as "chickweed", or Stellariomedia, but as used throughout the specification and the claims the term "chickweed" is intended to encompass the entire Pink family.

Pansy (Viola tricolor) which has a number of subvarieties belongs to the family of Violaceae (hereinafter collectively referred to in the specification and the claims by the shorthand expression "pansy"), and its drug is the above ground part of the plant collected in time of flowering. The main active ingredients of the drug are violaquercetin, flavone glycoside, quercetin glycone, violanin anthocyan glycoside, sugars, organic acids, methyl ester of salicylic acid, volatile oils.

The tea made from the drug is known for its expectorating, blood-clearing, hypotensive effects.

The skin regenerating cosmetic compositions of the present invention comprise as active ingredients a mixture of a skin regeneratingly effective amount of the extracts. As used throughout the specification and the claims, reference to a mixture of extracts includes both a mixture of extracts, as well as an extract of a mixture of the source plants of the same active ingredients. Thus the plant varieties can be extracted separately, and the extracts can be mixed when the composition is prepared, or the plants can be blended in a predetermined ratio before the extraction. Reference to a skin regeneratingly effective amount in connection with the active ingredients of the composition of the present invention covers all concentration ranges and synergistic ratios between the two actives, the skin regenerating efficacy of which can be routinely determined by objective and subjective criteria well known to those skilled in the field of dermatology and cosmetology. Suitably, the compositions of the present invention contain, and suitably consist essentially of, from about 3% to about 60% wt. based on the composition of the oily or aqueous and/or cosmetically acceptable organic solvent extracts of the drug of chickweed and pansy together with one or more of any otherwise conventional cosmetically acceptable vehicle, excipient, and supplementary material.

The compositions of the present invention contain the extracts of the chickweed and pansy suitably in a weight ratio between from about 7 to about 1 and from about 1 to about 7.

Aqueous, aqueous ethanolic, aqueous propylene glycolic, cosmetic petrolatum oily plant extracts can be used for preparing the compositions. The composition can suitably contain as a vehicle artificial or natural fats, oils, fatty alcohols, esters of fatty acids and/or the derivatives thereof.

Suitable excipients are thickening, epithelium regenerating, skin soothing, skin nourishing, tonic, antiseptic, moisturizing, solubilizing materials, stabilizers, preservatives, emulgeators, fillers, vitamins and fragrance, that are well known per se.

The composition can also contain supplementary materials, such as light protecting materials, for example octylmethoxy cinnamate.

The plant extracts can be prepared in any customary manner, such as diffusion extraction, steeping, circulation extraction, or counter-current extraction. In these cases, the drug bearing parts of the plants are optionally dried, then crushed and extracted suitably with from about 2 to about 30 times the weight of extracting agent based on the amount of dried plant parts.

The extraction is carried out suitably between about 15° C. and the boiling point of the extracting agent, by steeping the plant for 2–3 days, or by countercurrent extraction for 1 hour. As is well known, in determining the efficacy of the extraction, the higher the temperature of the extraction the shorter need be the duration thereof.

In case of large scale processing suitably the plant is extracted at a higher temperature during a shorter time period, and whenever possible, the extraction and solvent recovery are carried out at the same time.

The synergetic effect of the composition according to the present invention was examined, and the details are described in the following illustrative preparation, compounding, and comparative examples, and are summarized in the table at the end.

EXTRACTION PREPARATION EXAMPLES

Example 1

One kg of dried, crushed drug of pansy was washed with water, then soaked in 2 kg of deionized water at room temperature for 2 days, with occasional stirring. The mixture was then filtered.

Example 2

One kg of dried, crushed drug of pansy was washed with water, then extracted with 30 kg of water at 90° C. for 30 minutes in an extractor. After cooling the extract was filtered. The solution obtained was tyndalled by heating it for 3 days, once each day to 80 ° C. for 1 hour.

Example 3

The process described in Example 1 was followed, but water containing 30% by volume of propylene glycol was used for soaking.

Example 4

One kg of dried, crushed, washed drug of pansy was extracted with 10 kg of 70% by volume aqueous ethanol for 10 hours at 40° C., under stirring. The extract obtained was filtered.

Example 5

One kg of dried, crushed, washed drug of pansy was extracted with 15 kg of cosmetic vaseline oil at 20 ° C. for 2 days, stirring the mixture several times. The plant pieces were removed by centrifuging, then the oily part was filtered.

Example 6

The process described in Example 1 was followed, but the drug of chickweed was extracted instead of the drug of pansy.

Example 7

The process described in Example 2 was followed, but the drug of chickweed was extracted instead of the drug of pansy.

Example 8

The process described in Example 1 was followed, but the drug of chickweed was extracted instead of the drug of pansy, with 2 kg of water containing 10% by volume propylene glycol.

Example 9

The process described in Example 4 was followed, but the drug of chickweed was extracted instead of the drug of pansy, with 50% by volume aqueous ethanol.

Example 10

The process described in Example 5 was followed, but the drug of chickweed was extracted instead of the drug of pansy.

Example 11

0,5 kg drug of pansy and 0,5 kg drug of chickweed was mixed, then thoroughly washed with water and extracted with 8 kg of water at 90° C. for 50 minutes in a countercurrent extractor. The solid part and liquid phase were separated by filtration.

COMPOUNDING EXAMPLES

Example 12. Emulsion

| | |
|---|---|
| Aqueous pansy extract obtained in Example 1 | 2.62 g |
| Aqueous chickweed extract obtained in Example 6 | 0.38 g |
| Hydrogenated castor oil | 6 g |
| Avocado oil | 4 g |
| Maize germ oil | 3 g |
| Mineral oil | 14 g |
| Cetyl alcohol | 1 g |
| Propylene glycol | 4 g |
| Vitamin A | 0.05 g |
| Vitamin E | 0.07 g |
| Preservative | 0.1 g |
| Fragrance | 0.1 g |
| Deionized water q.v. 100.00 g | |

Example 13. Nourishing Night Cream

| | |
|---|---|
| Aqueous pansy extract obtained in Example 2 | 7.5 g |
| Aqueous chickweed extract obtained in Example 7 | 52.5 g |
| Hydrogenated castor oil | 10 g |
| Petrolatum | 5 g |
| Lanette N* | 2 g |
| Avocado oil | 10 g |
| Mineral oil | 4 g |
| Wheat germ oil | 5 g |
| Cholesterol | 2.6 g |
| Glycerol | 0.5 g |
| Vitamin A | 0.05 g |
| Vitamin E | 0.05 g |
| Preservative | 0.1 g |
| Fragrance | 0.1 g |
| Deionized water q.v. 100 g | |

* A mixture of sodium cetyl-stearyl sulfate and cetyl-stearyl alcohol, sold by Henkel AG)

Example 14. Night Face Creme

| | |
|---|---|
| Oily pansy extract obtained in Example 5 | 10 g |
| Oily chickweed extract obtained in Example 10 | 10 g |
| Cutina MD[1] | 4 g |
| Stearyl alcohol | 8 g |
| Emulgin B1[4] | 1.5 g |
| Emulgin B2[2] | 1.5 g |
| Eutanol G[3] | 15 g |
| Cutina BW[5] | 2 g |
| Triethanolamine | 0.2 g |
| Deionized water | 47.8 g |

[1] A mixture of mono-and diglycerides of palmitic and stearic acids sold by Henkel AG.
[2] A cetyl; stearyl alcohol sold by Henkel AG.
[3] 2-octyl-dodecanol sold by Henkel AG.
[4] A cetyl-stearyl-alcohol sold by Henkel AG.
[5] Partial glyceride and ester of long chain fatty acids sold by Henkel AG.

Example 15. Facial Tonic

| | |
|---|---|
| Ethanolic pansy extract obtained in Example 4 | 25 g |
| Ethanolic chickweed extract obtained in Ex. 9 | 15 g |
| Glycero | 2 g |
| Allantoin | 0.2 g |
| Cetiol HE* | 2 g |
| Ethanol 96% vol. | 5.2 g |
| Deionized water qv. 100 g | |

*Polyethylene glycol-7-glycerylcocate, coco fatty acid sold by Henkel AG.

Example 16. Liquid Cleansing Emulsion

| | |
|---|---|
| Propylene glycolic pansy extract obtained in Example 3 | 9 g |
| Propylene glycolic chickweed extract obtained in Ex. 8 | 11 g |
| Texapon EVR* | 40 g |
| Texapon N 40* | 40 g |

*Sodium lauryl-ether sulfate sold by Henkel AG (with additional ingredients in the case of Texapon EVR).

Example 17. Light Protection Emulsion

| | |
|---|---|
| Aqueous extract obtained in Example 11 | 30 g |
| Glycerol-sorbitan-hydroxy-isostearate | 5 g |
| Isopropyl myristate | 5 g |
| Cyclic dimethyl-polysiloxane | 3 g |
| Polyoxyethylene stearyl-stearate | 4 g |
| Propylene glycol | 2 g |
| Ethoxylated, hydrogenated castor oil | 0.5 g |
| Hydrogenated castor oil | 0.7 g |
| Fragrance | 0.1 g |
| Olive oil | 10 g |
| Octyl-methoxy-cinnamate | 0.2 g |
| Deionized water qv. 100 g | |

Example 18. Body Lotion

| | |
|---|---|
| Extract obtained in Example 3 | 2 g |
| Extract obtained in Example 8 | 2 g |
| Polyglyceryl-3-dioleate | 4 g |
| White petrolatum | 10 g |
| Paraffin wax | 2 g |
| Paraffine, microcrystalline | 2 g |
| Alfa-bisabolol | 0.2 g |
| Dichloro-benzyl alcohol | 0.1 g |
| Cetearyl octanoate | 8 g |
| Magnesium sulfate heptahydrate | 0.7 g |
| Allantoin | 0.4 g |
| Imidazolidnyl urea | 0.3 g |
| Deionized water q.v. 100 g | |

Example 19. Face Peeling Mask

| | |
|---|---|
| Aqueous extract obtained in Example 11 | 25 g |
| Cetyl-stearyl alcohol | 10 g |
| Paraffin oil | 10 g |
| Almond oil | 3 g |
| Myristyl-ethoxy-myristate | 2 g |
| Apricot kernel powder | 2 g |
| Allantoin | 0.2 g |
| Seppicide HB* | 0.3 g |
| Fragrance | 0.2 g |
| Deionized water q.v. 100 g | |

*Methyl-, ethyl-, propyl-, butylparaben and phenoxy-ethanol sold by Seppic.

COMPARATIVE EXAMPLES AND CONTROLS

Control 1

The composition of Example 18 was prepared, but instead of pansy extract the same quantity of deionized water was used. The composition was examined on 25 women and 5 men aged from 30 to 55 years. The face skin of the treated persons was dr,/, slightly inflamed, scurfy and in some cases manifesting pruritus. The composition was applied twice a day for two weeks. After this period the effect was evaluated and the following results were obtained:

in 13 cases no change was observed, in 7 cases the desquamation and pruritus were lessened, in 6 cases the desquamation, pruritus and inflammation were lessened, but the skin was dry, in 4 cases the complaints were eliminated.

Control 2

The composition of Example 18 was prepared, but instead of chickweed extract the same quantity of deionized water was used. The composition was examined on 24 women and 6 men aged from 32 to 58 years. The symptoms, the treatment and the way of evaluation was the same as described in Control 1. The following results were obtained:

in 14 cases no change was observed, in 5 cases the inflammation and pruritus were lessened, but the skin was dry and scurfy, in 8 cases the inflammation and desquamation was significantly lessening, but pruritus was manifested and the skin was dry, in 3 cases the complaints were eliminated.

Control 3

The composition of Example 18 was prepared, but deionized water was used instead of the two plant extracts. The composition was examined on 27 women and 3 men aged from 33 to 57 years. The symptoms, the treatment and the way of evaluation was the same as described in Control 1. The following results were obtained:

in 25 cases the symptoms remained the same, in 4 cases inflammation was hardly observable, dryness and desquamation were slightly lessened.

in 1 case all the symptoms were lessened to about ½ intensity.

Example 20

The composition of Example 18 was examined on 26 women and 4 men aged from 31 to 60 years. The symptoms, the treatment and the way of evaluation was the same as described in Control 1. The following results were obtained:

in 1 case the symptoms were not lessened, in 2 cases a small degree of inflammation, dryness, desquamation could be observed, in 4 cases the inflammation and pruritus were lessened to a small extent, while the dryness and desquamation were lessened to a larger extent.

in 23 cases the treated persons became asymptomatic.

TABLE

Summary of the results obtained in Controls 1–3 and Example 20
(%, based on the sample of 30 persons)

| Example No. | No effect was observed | Effect of the composition | | |
|---|---|---|---|---|
| | | weak | medium | good |
| Control 1 | 43 | 23 | 20 | 14 |
| Control 2 | 46 | 17 | 27 | 10 |
| Control 3 | 83 | 14 | 3 | — |
| Example 6 | 3 | 7 | 13 | 77 |

We claim:

1. A skin regenerating composition which comprises as active ingredients a mixture of each of an extract of the plants chickweed and pansy from about 3% wt. to about 60% wt. based on the composition.

2. The skin regenerating composition of claim 1, wherein said extract is an extract with one or more of oil, water, and a cosmetically acceptable organic solvent, the composition further comprising from about 40% wt. to about 97% wt. based on the composition of one or more of a cosmetically acceptable vehicle, excipient, and supplementary material.

3. The skin regenerating composition of claim 1, wherein the weight ratio of extracts of each of the active ingredient plants is between from about 7 to about 1 and from about 1 to about 7.

4. The skin regenerating composition of claim 1, wherein said extracts are extracts in water.

5. The skin regenerating composition of claim 1, wherein said extracts are extracts in aqueous ethanol.

6. The skin regenerating composition of claim 1, wherein said extracts are extracts in aqueous propylene glycol.

7. The skin regenerating composition of claim 1, wherein said extracts are extracts in mineral oil.

8. The skin regenerating composition of claim 2, wherein said carrier is one or more of a cosmetically acceptable natural fat, oil, fatty alcohol, fatty acid ester.

9. The skin regenerating composition of claim 2, wherein said excipient is one or more thickening, epithelium regenerating, skin soothing, skin nourishing, tonic, antiseptic, moisturizing, solubilizing materials, stabilizers, preservatives, emulgeators, fillers, vitamins or fragrance.

10. The skin regenerating composition of claim 2, wherein said supplementary material is a material for protecting the composition against the effect of exposure to light.

11. The skin regenerating composition of claim 10, wherein said supplementary material is octyl methoxyinnanate.

* * * * *